United States Patent [19]

Kolodny et al.

[11] Patent Number: 5,674,690
[45] Date of Patent: Oct. 7, 1997

[54] METHODS OF DIAGNOSIS, MONITORING AND STAGING OF VARIOUS CONDITIONS USING IGG ANTIBODIES AGAINST HYDROXY-FATTY ACID CONTAINING SULFATIDE

[75] Inventors: Edwin H. Kolodny, New York, N.Y.; Srinavasa Raghavan, North Brunswick, N.J.; Miguel Angel Gama Sosa; Rita De Gasperi, both of New York, N.Y.

[73] Assignee: New York University, New York, N.Y.

[21] Appl. No.: 536,940

[22] Filed: Sep. 29, 1995

Related U.S. Application Data

[63] Continuation-in-part of Ser. No. 444,260, May 18, 1995, abandoned, which is a continuation of Ser. No. 957,552, Oct. 8, 1992, abandoned.

[51] Int. Cl.$^6$ ................ G01N 33/53; G01N 33/537; G01N 33/543; G01N 33/564
[52] U.S. Cl. ................ 435/7.1; 435/7.92; 436/506; 436/63; 424/130.1
[58] Field of Search ................ 424/130.1; 435/7.1, 435/7.92; 436/506, 63

[56] References Cited

U.S. PATENT DOCUMENTS 4,661,586  4/1987  Levy et al. ................ 530/387

OTHER PUBLICATIONS

De Gasperi et al, "Intrathecal synthesis of anti-sulfatide IgG is associated with peripheral nerve disease in acquired immunodeficiency syndrome" Aids Research and Human Retroviruses, vol. 12, No. 3, pp. 205–211 Feb. 1996.

Arioglu et al, "Anti-sulfatide antibodies in SLE", J. Invest. Medicine, vol. 43, suppl. 2, p. 284A 1995.

Buschard et al, "Sulphatide and suphatide antibodies in insulin-dependent diabetes mellitus", The Lancet, vol. 342, p. 840 Oct. 2, 1993.

van Vliet et al, "Antibodies against glycosphingolipids in sera of patients with idiopathic thrombocytopenic purpura", Br. J. Haematology, vol. 67, pp. 103–108 Sep. 1, 1987.

Pestronk et al, "Polyneuropathy syndromes associated with serum antibodies to sulfatide and myelin–associated glycoprotein" Neurology, vol. 41, pp. 357–362 Mar. 1991.

Fredman et al, "Antibodies in sera from patients with inflammatory demyelinating polyradiculneuropathy react with ganglioside LM1 and sulphatide of peripheral nerve myelin" J. of Neurology, vol. 238, pp. 75–79 Jun. 1991.

Aotsuka et al, "Antibodies against sulphatide in sera from patients with autoimmune rheumatic disease" Clin. Exp. Immunol. vol. 87, pp. 438–443 1992.

Chou, Denise K.H., "Structure of Sulfated Glucuronyl Glycolipids in the Nervous System Reacting with HNK–1 Antibody and some IgM Paraproteins in Neuropathy", The Journal of Bilogical Chemistry, vol. 261, No. 25, pp. 11717–11725 (1986).

Pestronk, A. et al., "Polyneuropathy Syndromes associated with Serum Antibodies to Sulfatide and Myelin–Associated Glycoprotein", NEUROLOGY, vol. 41, pp. 357–362 (1991).

Toda, G. et al., "Hepatocyte Plasma Membrane Glycophingolipid Reactive with Sera from Patients with Autoimmune Chronic Active Hepatitis: Its Identification as Sulfate." HEPATOLOGY, vol. 12, No. 4, pp. 664–670 (1990).

Ilyas et al., "Antibodies to sulfated glycolipids in Gullian-Barre syndrome (GBS)", Journal Neurological Science, vol. 105, No. 1, pp. 108–117 (1991).

Potocnjak et al., "Inhibition of Idiotype–anti–idiotype interaction for detention of a parasite antigen: a new immunoassay", Science, vol. 215, pp. 1637–1639 (1982).

Miller et al., "The Management of AIDS Patients.", MacMillan Press, London, pp. 23–33 (1986).

Albers et al. "Basic Neurochemistry.", Little, Brown & Co., London, pp. 209, 376–378 (1992).

Quattrin et al., Journal Neurological Science, vol. 112, pp. 152–159 (1992).

Gregoriadis et al., Trends in Biotechnology, vol. 11, pp. 440–442 (1993).

Kikkawa et al., Nippon Jinzo Gakkai Shi, vol. 33, No. 7, pp. 635–642 (1991).

Baba et al., "A Human Monoclonal Antibody derived from axillary nodes of a breast cancer patient reactive to a sulfated glycolipid.", HYBRIDOMA, vol. 11, No. 2, pp. 107–119 (1992).

Handa et al., "Inhibtion of infection with human immudeficiency virus type 1 by sulfated gangliosides.", Bichemical and Biophysical Research Communications, vol. 175, No. 1, pp. 1–9 (1991).

Sadiq et al., "Sulfatide may be a neuronal receptor for HIV", Neurology, vol. 42, No. 3, p. 236 (1992).

*Primary Examiner*—Lila Feisee
*Assistant Examiner*—Yvonne Eyler
*Attorney, Agent, or Firm*—Browdy and Neimark

[57] ABSTRACT

A method for screening for, diagnosing, monitoring or staging of multiple sclerosis, HIV infection, rheumatoid arthritis or systemic lupus erythematosus in a subject, is based on the detection of IgG antibodies against the hydroxy-fatty acid form of sulfatide in a tissue or body fluid sample of the subject. The presence of such IgG levels substantially above those in healthy controls is indicative of an increased likelihood that the subject has one of such conditions.

15 Claims, 6 Drawing Sheets

GALACTOSYLCERAMIDE

SULFATIDE

LACTOSYLCERAMIDE 3-SULPHATE

SEMINOLIPID

LYSOSYLPHATIDE

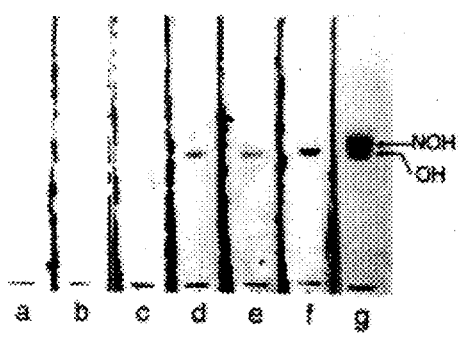 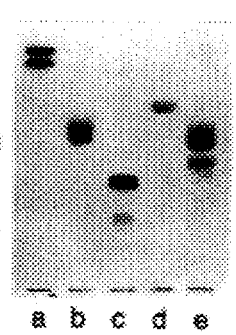 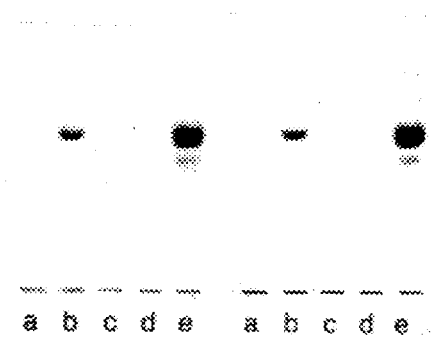
FIG.10A   FIG.10B   FIG.10C   FIG.10D

METHODS OF DIAGNOSIS, MONITORING AND STAGING OF VARIOUS CONDITIONS USING IGG ANTIBODIES AGAINST HYDROXY-FATTY ACID CONTAINING SULFATIDE

CROSS-REFERENCE TO RELATED APPLICATIONS

The present application is a continuation-in-part of application Ser. No. 08/444,260, filed May 18, 1995, now abandoned which is a continuation of application Ser. No. 07/957,552, filed Oct. 8, 1992, now abandoned the entire contents of both of which being hereby incorporated herein by reference.

FIELD OF THE INVENTION

The present invention relates to methods of screening for, diagnosing the presence of, or monitoring or staging the course or severity of various conditions by detecting the presence of IgG antibodies against the hydroxy-fatty acid-containing form of sulfatide in body fluids of such individuals, and more particularly to methods of screening for or diagnosing the presence of multiple sclerosis (MS), HIV infection, rheumatoid arthritis (RA) or systemic lupus erythematosus (SLE) in subjects suspected of having such conditions, or for monitoring or staging the course or severity of MS, RA or SLE by such detection.

BACKGROUND OF THE INVENTION

Multiple sclerosis is one of the most common neurological diseases. It affects primarily young adults causing visual symptoms, gait disorders, limb weakness, sensory disturbances and bowel and bladder dysfunctions. Recurrent exacerbations of brain white matter disease disable an individual in a stepwise fashion leading to a chronically dependent condition.

Several lines of research point to autoimmune mechanisms as responsible for the demyelination that is present in patients with this disease. Treatment with steroids and other immunosuppressive compounds often ameliorate the signs and symptoms of the disease. Several reports have suggested a role for antiglycolipid antibodies in neurodegenerative disorders. See Fredman et al., *J. Neurol.*, 238:75–79 (1991); Quattrini et al., *J. Neurol. Sci.*, 112:152–159 (1992); Pestronk et al., *Neurology*, 41:357–362 (1991); Ilyas et al., *J. Neurol Sci.*, 105:108–11 (1991); and Ryberg, *J. Neurol. Sci.*, 38:357–382 (1978). It is useful to have as many means as possible for diagnosing and/or monitoring conditions such as multiple sclerosis.

HIV infection is accompanied by neurological disorders affecting both the central nervous system (CNS) and the peripheral nervous system (PNS) (Simpson et al., *Ann Intern. Med.*, 121:769–785 (1994)). A characteristic feature of the nervous system pathology in HIV infection is myelin breakdown. See Simpson et al. (1994), supra; Rhodes, *Hum. Pathol.*, 18:636–643 (1987); Budka, *Brain Pathol.*, 1:163–175 (1991); Shaver, *J. Neuropathol. Exp. Neurol.*, 51:3–11 (1992); and Kleihues et al., *Acta. Neuropathol.*, 68:333–339 (1985). In HIV leukoencephalo-pathy diffuse white matter damage including myelin loss, reactive astrogliosis and appearance of scattered multi-nucleated giant cells can be observed (Kleihues et al. (1985), supra). To date there is no widely held consensus on the etiology of demyelination or other neurological complications associated with HIV infection. Proposed mechanisms include direct viral infection of myelin and neuronal cells, release of toxic viral proteins and cytokines from infected monocytes and macrophages, and the induction of autoantibodies (Barnes, *Science*, 235:1574–1577 (1987); Tillman et al., *Seminars in the Neurosciences*, 3:131–139 (1991); Epstein et al., *Ann. Neurol.*, 33:429–436 (1993); Solinger et al., *Rheum, Dis. Clin. North Am.*, 17:157–176 (1991)). A variety of autoantibodies directed against nucleoantigens, cardiolipin, actin, collagen, platelets, erythrocytes, lymphocytes and neutrophils have been detected in the sera of HIV$^+$ individuals (Solinger et al (1991), supra). Moreover, antibodies against cerebellar soluble lectin (CSL) and myelin basic protein have also been described in the CSL of AIDS patients (Hagberg et al., *J. Neuroimmunol.*, 36:245–249 (1992); Saida et al., *Science*, 204:1103–1106 (1979)).

Studies in rabbits have shown that penetration of antibodies directed against the myelin component and glycolipid hapten galactosylceramide (see FIG. 1 for structure) across the blood brain barrier results in PNS demyelination (Saida et al. (1979), supra). PNS demyelination, in turn, is manifested by tremulousness, ataxia, flaccid paresis and limb hypesthesia (Saida et al., *Ann. Neurol.*, 9:87–101 (1981)). Otherwise, rabbits with high titers of circulating anti-galactosylceramide antibodies did not show demyelination, which suggested that the blood brain barrier is protective from the antibody damages (Ozawa et al., *Acta. Neuropathol.*, 77:621–628 (1989)).

Additional means of diagnosis of HIV infection and the development of PNS disease associated with HIV infection are always useful.

Rheumatoid arthritis and systemic lupus erythematosus are classified as autoimmune diseases where the lining of joints (in RA) and the connective tissues (in SLE) are affected. These diseases have been found to be associated with the aberrant expression of human lymphocyte antigen (HLA) in tissues where they normally do not appear, such as in the joint lining.

As leukocytes penetrate the synovial lining of the joints to cause an autoimmune response in RA, affected joints become stiff, sore and swollen. Joint immobility and permanent deformity may result from chronic RA. Rheumatoid factor (RF) is found in the sera and synovial fluid of adult patients with established rheumatoid arthritis.

In the progression of the disease, SLE is capable of attacking all soft internal organs as well as the bones and muscles. This autoimmune disease generally manifests itself at the initial stage with a characteristic skin rash on the forehead and cheeks. Other common manifestations include hair loss, arthritis, severe kidney damage, inflammation of the lining of the lungs, accumulation of fluid around the heart, and inflammation of blood vessels in the brain.

Once RA or SLE has begun, the autoimmune diseases are usually associated with alternating periods of deterioration and remission.

Myelin is characterized by a low amount of water, low protein and a high lipid content. The solids of myelin are 70–80% lipid and 20–30% protein; the lipids of mammalian CNS myelin are composed of 25–28% cholesterol, 27–30% galactosphingolipid, and 40–45% phospholipid (*Basic Neurochemistry*, Alheus, et al., eds., Little, Brown and Co., Boston, 1st Ed. (1972), page 376). Table 1 lists the composition of bovine, rat and human myelin compared to bovine and human white matter, human gray matter and rat whole brain. It can be seen that all the lipids found in whole brain are also present in myelin.

TABLE 1

Composition of CNS Myelin and Brain[a]

| Substance[b] | Myelin | | | White Matter | | Gray Matter | Whole Brain |
|---|---|---|---|---|---|---|---|
| | Human | Bovine | Rat | Human | Bovine | (Human) | (Rat) |
| Protein | 30.0 | 24.7 | 29.5 | 39.0 | 39.5 | 55.3 | 56.9 |
| Lipid | 70.0 | 75.3 | 70.5 | 54.9 | 55.0 | 32.7 | 37.0 |
| Cholesterol | 27.7 | 28.1 | 27.3 | 27.5 | 23.6 | 22.0 | 23.0 |
| Cerebroside | 22.7 | 24.0 | 23.7 | 19.8 | 22.5 | 5.4 | 14.6 |
| Sulfatide | 3.8 | 3.6 | 7.1 | 5.4 | 5.0 | 1.7 | 4.8 |
| Total galactolipid | 27.5 | 29.3 | 31.5 | 26.4 | 28.6 | 7.3 | 21.3 |
| Ethanolamine phosphatides | 15.6 | 17.4 | 16.7 | 14.9 | 13.6 | 22.7 | 19.8 |
| Lecithin | 11.2 | 10.9 | 11.3 | 12.8 | 12.9 | 26.7 | 22.0 |
| Sphingomyelin | 7.9 | 7.1 | 3.2 | 7.7 | 6.7 | 6.9 | 3.8 |
| Phosphatidylserine | 4.8 | 6.5 | 7.0 | 7.9 | 11.4 | 8.7 | 7.2 |
| Phosphatidylinositol | 0.6 | 0.8 | 1.2 | 0.9 | 0.9 | 2.7 | 2.4 |
| Plasmalogens[c] | 12.3 | 14.1 | 14.1 | 11.2 | 12.2 | 8.8 | 11.6 |
| Total phospholipid | 43.1 | 43.0 | 44.0 | 45.9 | 46.3 | 69.5 | 57.6 |

[a]From W. Norton, in G. J. Siegel et al (eds), Basic Neurochemistry, 3rd ed., Boston: Little, Brown, 1981, p. 77.
[b]Protein and lipid figures in % dry weight; all others in % total lipid weight.
[c]Plasmalogens are primarily ethanolamine phosphatides.

Sulfatide is galactosylcerebroside esterfied to sulfate at the 3' position of the galactose moiety (see FIG. 1 for structure). Many different fatty acids are formed in cerebrosides and sulfatides, as well as in other sphingolipids. Cerebrosides generally contain very long chain normal (lignoceric (24:0) and nervonic (14:1 ($\omega$-9))), $\alpha$-hydroxy (cerebronic (24h:0)), and odd number (23:0, 23h:0) fatty acids (Agranoff et al., in Basic Neurochemistry: Molecular, Cellular and Medical Aspects, Siegel et al., eds., Raven Press, New York, 5th Edition, 1994, pp. 97–116). The fatty acid patterns of cerebrosides and sulfatides are the same in cerebral cortex as in white matter, varying only slightly with maturation of the brain. The percentage of 2-hydroxy acids increases slightly, from 50% at birth to 60% at 2 years of age for cerebrosides and from 20% to 35% for sulfatides (Svennerholm et al., Brain Research, 55:413–423 (1973)).

Antibodies against sulfatide have been found in some patients with a few specific autoimmune chronic liver diseases (Toda et al., Hepatology, 12:664–670 (1990)) and in patients with certain forms of polyneuropathy (Pestronk et al., Neurology, 41:357–362 (1991)). Ryberg (1978), supra, reported the presence of antisulfatide IgG in one serum and one cerebrospinal fluid (CSF) from two different MS patients out of a total of 60 MS patients tested. The single serum antibody sample found was also tested by complement fixation against both forms of sulfatide separated by conventional chromatography techniques, and was found to be reactive with both the hydroxy fatty acid and non-hydroxy fatty acid forms of sulfatide. The highly non-specific results of Ryberg do not suggest that the presence of IgG antibodies preferential to the hydroxy fatty acid form of sulfatides can serve as a diagnosis of an increased likelihood that the subject tested has MS.

Quattrini (1992), supra, reported increased anti-sulfatide antibody titers in one of 17 subjects with MS. The increased titer was selective for IgM lambda. No increase in IgG titer was detected. This research was performed using an ELISA technology and only used thin layer chromatography (TLC) immuno-staining to confirm the positive serum.

Ilyas reports a study in which human sera is assayed for the presence of antisulfatide antibodies to determine if there is a correlation between antisulfatide antibodies and various neurological diseases. Sera were tested from 53 patients with acute Guillain-Barré syndrome (GBS), 15 patients with chronic inflammatory demyelinating polyneuropathy (CIDP), 13 patients with other neurological diseases (OND), 33 patients with non-neurological inflammatory, infections, allergic or autoimmune (IIAA) diseases (including four with HIV infection), and 31 healthy control subjects. The sera were screened for the presence of antibody by ELISA and by TLC overlay. The values of anti-sulfatide IgM and IgG were not elevated as compared to disease and healthy control sera. However, sera from 11 of 53 GBS patients had anti-sulfatide IgM levels that were more than 2 SD above the mean of the healthy control group as compared to 6 of 92 disease and healthy controls. Only 5 of 53 GBS sera had elevated levels of anti-sulfatide IgG. Four of 31 IIAA patients showed elevated anti-sulfatide IgG antibodies, but there was no report of which IIAA patients had such elevated levels, i.e., whether or not the anti-sulfatide antibody titers were raised for the HIV patients was not reported. The TLC tests conducted for certain sera found positive in the ELISA test did not indicate whether or not there was a preference to either fatty acid form of sulfatide, although it was noted that even antibodies which reacted very strongly with sulfatide in ELISA did not react with sulfatide on TLC until more than 10 µg of sulfatide was loaded.

Fredman conducted TLC-ELISA assays for anti-sulfatide antibodies in the sera of 23 patients with GBS, 15 patients with CIDP, and 40 healthy controls. Antibodies to sulfatide were observed in 65% and 87% of the sera from patients with GBS and CIDP, respectively, but only in 15% of the control sera. The antibodies to sulfatide were all IgG. In the control both IgM and IgG anti-sulfatide antibodies were detected. No distinction between the fatty acid form of sulfatide was drawn other than to recognize that in the materials used, the sulfatide contained 20% hydroxy acids.

Other reports have shown the presence of serum antisulfatide antibodies in patients with autoimmune rheumatic disease (Aotsuka et al., Clin. Exptl. Immunol., 87:438–443 (1992)), idiopathic thrombocytopenia purpura (Van Vleet et al., Brit. J. Haematol., 67:103–108 (1987)), kidney diseases (Kikkawa et al., Nippon Jinzo Gakkai Shi, 33:635–642 (1991) and Tamaoki et al., Nippon Jinzo Gakkai Ski, 33:1054 (1991)), and diabetes (Buschard et al., *Lancet*, 342:840 (1993)).

Murakami et al, *J. Biol. Chem.*, 266:15414–15419 (1991), disclose obtaining a human monoclonal antibody derived from the lymphocytes of a lupus patient with thrombocytopenia. This antibody reacted with single stranded DNA and platelets. It was determined that the structure of the platelet component that is the antigen target of this monoclonal antibody is a monogalactosyl sulfatide.

SUMMARY OF THE INVENTION

It has now been discovered that IgG antibodies preferential to the hydroxy fatty acid form of sulfatide appear in patients with various conditions, specifically including MS patients, HIV infected patients, RA patients and SLE patients. A polyclonal antibody which preferentially reacts with the hydroxy fatty acid containing form of sulfatide and which is of IgG immunotype appears in the serum and other antibody containing fluids and tissues of patients having such conditions.

In order for the assay to be as selective and specific as possible, it is important that the assay be conducted under conditions which do not degrade the results. For example, assay methods which result in high levels of background binding render the results inaccurate and difficult to interpret. It is believed that this is one reason why certain prior art experiments appear to be substantially less selective for patients with MS and HIV infection. It is thought that this is due to the fact that conventional ELISA assays are conducted on plastic substrates and either the sulfatide antibodies might react with the plastic, or other endogenous antibodies present may react with the blocking agent (usually bovine serum albumin) giving a false positive result, or both.

One way to avoid such high levels of background binding is to use the high performance thin layer chromatography (HPTLC) immunostaining technique. This technique has the further advantage of permitting one to specifically identify preferential binding of the antisulfatide IgG reactivity toward the hydroxy fatty acid form of sulfatide as opposed to the non-hydroxy fatty acid form thereof, even in the presence of antibodies against the blocking agent.

By means of the assay of the present invention, in a large sampling (178) of multiple sclerosis patients, 83% (143) showed higher levels of antisulfatide IgG specific for the hydroxy fatty acid form of sulfatide, as compared to control populations. Furthermore, 33 out of 37 HIV-1$^+$ individuals (89%) tested positive for the presence of serum antisulfatide IgG specific for the hydroxy fatty acid form of sulfatide at a 1:1,000 dilution. In contrast, only 16% of asymptomatic HIV$^-$ controls tested positive for the same antibody at the same dilution. High levels of specificity for RA and SLE were also found. These results are unexpected in light of the prior art experiments discussed above. The preferential specificity for the hydroxy fatty acid form of sulfatide could not have been predicted and provides another layer of specificity to the assay of the present invention. Furthermore, the specific results with respect to multiple sclerosis, HIV infection, rheumatoid arthritis and SLE could not have been predicted from the experiments which had previously been reported in the prior art.

BRIEF DESCRIPTION OF THE DRAWINGS

FIGS. 10A–D show the results of TLC immunostaining. FIG. 10A shows the reactivity of control (lanes a–c) and HIV$^+$ sera (lanes d–f) with sulfatide. In lane g, sulfatide was chemically stained with orcinol. NOH and OH indicate the non-hydroxy and hydroxy forms of sulfatide respectively. FIGS. 10B, C and D show the specificity of the antisulfatide IgG against several glycolipids. FIG. 10B shows the chemical staining with orcinol while FIGS. 10C and D show the immunostaining using serum from an HIV$^+$ individual and affinity purified antisulfatide IgG respectively. Lane a, galactosylceramide; lane b, bovine brain sulfatide; lane c, lysosulfatide; lane d, seminolipid; lane e, urine sulfatide (upper band) and lactosylceramide sulfate (lower band).

DETAILED DESCRIPTION OF PREFERRED EMBODIMENTS

Figure 1:
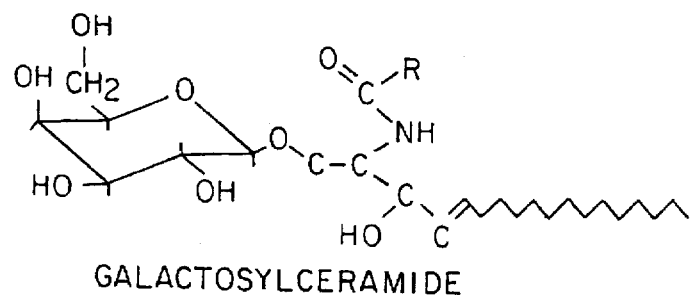
FIG. 1 shows the structural formulas of various glycolipids.
Figure 1:
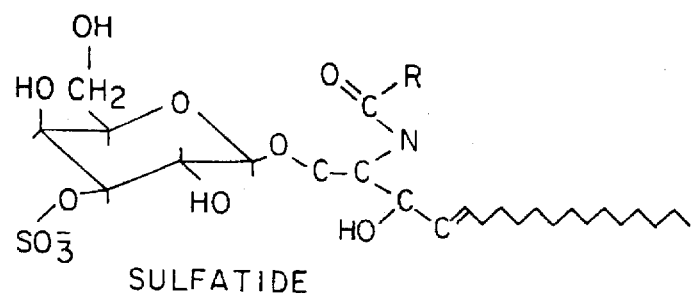
Figure 1:
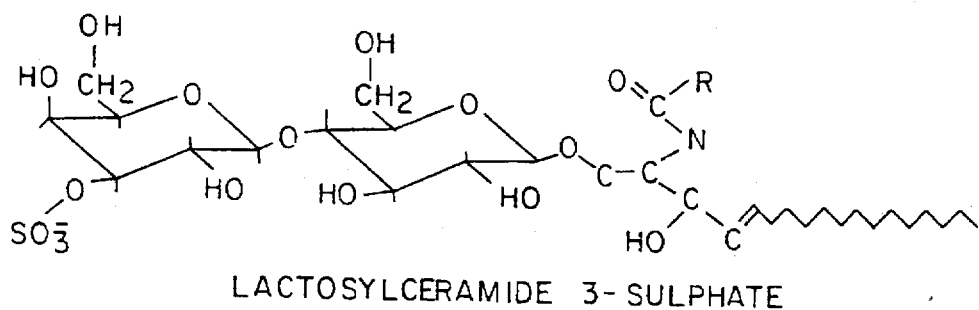
Figure 1:
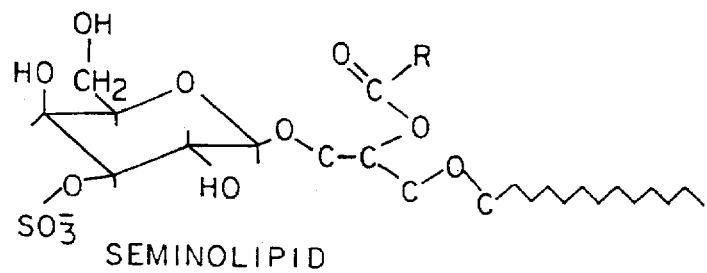
Figure 1:
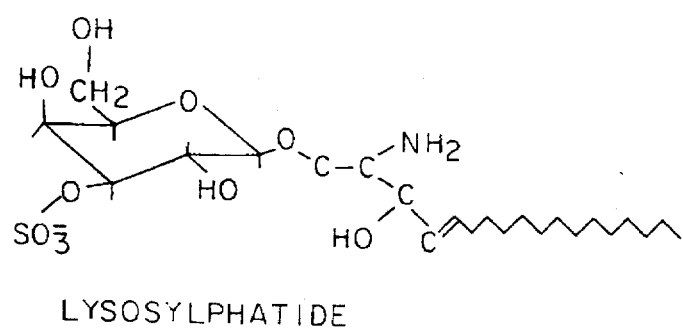

It has now been discovered that the body fluids of patients having various conditions, particularly including multiple sclerosis, HIV-1 infection, rheumatoid arthritis, or SEE, contain IgG antibodies specific for the hydroxy fatty acid form of sulfatide, while healthy HIV-1 negative individuals with no neurological degeneration lack substantial amounts of such antibodies. Accordingly, assay methods have been developed for diagnosing patients having such conditions which can be routinely accomplished using known method steps based on the teachings and guidance presented herein without undue experimentation.

Body fluid or tissue samples, or extracts thereof, of individuals suspected of having such conditions, may include sera, CSF, urine, lymphatic fluid, saliva and tears.

According to methods of the present invention, the specified antibodies can be detected in a sample of a body fluid of an individual by showing preferential reactivity towards the hydroxy-fatty acid-containing form of sulfatide or towards anti-idiotypic antibodies thereto, including chimeric antibodies, made according to known method steps; see, e.g., Harlow and Lane, *Antibodies: A Laboratory Manual*, Cold Spring Harbor Press, N.Y. (1988); and Ausubel et al., eds., *Current Protocols in Molecular Biology*, Wiley Interscience, N.Y. (1987; 1992); Sambrook et al. *Molecular Cloning: A Laboratory Manual.*, Second Edition, Cold Spring Harbor Press, N.Y. (1989) which are incorporated entirely herein by reference.

It is important that the assay conducted be able to specifically recognize antibodies against the hydroxy-fatty acid form of sulfatide. Sulfatide obtained from commercial sources such as from Sigma Chemical Company, St. Louis, Mo., or that obtained from the urine of patients with conditions known to secrete the sulfatide into the urine, such as late infantile metachromatic leukodystrophy, may be used as the source of sulfatide as long as some means is present to separate the fatty acid forms of the sulfatide so that preferential activity against the hydroxy-fatty acid form of sulfatide can be observed. HPTLC is an excellent technique for this purpose, although it is not the exclusive operable technique.

More selective results are obtained when assaying specifically for the IgG form of antibody. Thus, when immunostaining with either anti-IgG or anti-IgM as the second antibody, the results show that the greatest activity is with anti-IgG and a weaker reaction with anti-IgM. Thus, while the assay technique may be carried out using generic anti-immunoglobulin as the second antibody, the strongest and most selective results are obtained when using anti-IgG so as to specifically assay for the IgG form of antibody against the hydroxy-fatty acid-containing form of sulfatide.

The anti-sulfatide IgG found in the serum of MS and HIV seropositive, RA, and SLE patients reacts equally well with the hydroxy-fatty acid-containing fraction of bovine brain sulfatide and that of human sulfatide prepared from the urine of a patient with metachromatic leukodystrophy. It also recognizes lactosylceramide sulfate (see FIG. 1 for structure) and to a lesser extent sulfogalactosyldiglyceride (seminolipid) (see FIG. 1 for structure). It does not react with the nonsulfated parent compound galactosylceramide. No reaction is detected with lysosulfatide (see FIG. 1 for structure), indicating that the fatty acid is important for binding while changes in the type of lipid moiety, as in the seminolipid, greatly reduces but does not abolish the reactivity. Reactivity towards lactosylceramide sulfate in which the galactose is not directly attached to ceramide is due to the conformation of this glycolipid which brings the galactose-3-sulfate and the ceramide as close as in the surface molecule. No reactivity is detected with sulfoglucuronylparagloboside, a sulfated glycolipid found in PNS myelin. The anti-sulfatide moiety was recognized by anti-κ and anti-λ light chain antibodies, suggesting its polyclonal nature.

While a positive indication in the assay of the present invention for IgG antibodies against the hydroxy-fatty acid form of sulfatide does not guarantee that the subject has a condition such as multiple sclerosis, HIV infection, RA, or SLE the presence of such an IgG level substantially above that in healthy controls is indicative of an increased likelihood that the subject has or may develop MS, AIDS, RA or SLE. Other neurological or nephrological conditions may also cause the appearance of such antibodies in amounts greater than control. However, in patients suspected of having such a condition, the assay of the present invention serves as an additional form of diagnosis, as a very large percentage of MS patients, HIV positive patients, RA patients and SLE patients have such circulating antibodies in amounts significantly greater than in healthy controls. Furthermore, a positive result in a cold screening of individuals not suspected of having any condition will alert medical personnel of the probable existence of a condition which will warrant further diagnosis with a substantial likelihood that such condition may be MS, RA, or SLE or may indicate the possibility of HIV-1 infection.

The assay of IgG antibodies which are preferential for the hydroxy fatty acid form of sulfatide in patients undergoing treatment or about to undergo treatment for MS, HIV infection, RA or SLE may also be used to monitor or stage the course of the disease, thereby monitoring the course or the efficacy of the treatments. In most cases, the quantitative or semi-quantitative results of such an assay, and particularly the trend as to whether the titer of such antibodies is increasing or decreasing in a given patient, is a factor which is directly related to the efficacy or course of the treatment. Thus, as the condition is being ameliorated, the antisulfatide antibody titer will generally fall. Similarly, as the condition becomes worse, the antisulfatide antibody titer will be expected to increase. Accordingly, another embodiment of the present invention is the monitoring of treatment or the staging of the condition being treated by quantitative or semi-quantitative analysis of the results of assaying for IgG antisulfatide antibodies preferential to the hydroxy fatty acid form of antisulfatide.

Another utility for the assay of the present invention is in the testing of blood supplies. If a blood sample tests positive for the IgG antibody against the hydroxy-fatty acid form of sulfatide, the blood should be discarded as probably coming from an unhealthy source and thus possibly subject to an unacceptable risk factor for the potential recipient.

In order to determine whether or not the assay results are substantially above those in healthy controls, side-by-side comparisons with the sera from known healthy controls may be conducted for a qualitative determination. Quantitatively, samples were considered to be positive for anti-sulfatide antibodies when titers are equal or greater than either 1:1,000 or 1:100 for serum and cerebrospinal fluid, respectively.

While HPTLC on an aluminum backed Silica Gel SG60 HPTLC plate (Merck) is a preferred substrate for the assay of the present invention, the method of the present invention is not limited thereto. It is believed, however, that antisulfatide antibodies may be removed or their reactivity modified by certain plastics. Indeed, the sulfatide epitopes may be differentially exposed when adsorbed on plastic as compared to silica gel. Thus, the use of silica gel as the substrate is preferred in accordance with the present invention.

While the present invention is not limited to the HPTLC technique described in the present examples, it is known that some other techniques are substantially less effective and so steps should be taken to ensure that whatever technique is used, the results are not substantially different than that which would be obtained using the HPTLC technique of the present examples. Thus, for example, ELISA or other immunoassay techniques may be used with sulfatide antigens of defined hydroxy fatty acid composition obtained, for example, by chemical synthesis or by previous separation and purification from natural sources, possibly including a variation of the substrate or the blocking agent to avoid the non-specific binding which has been found to occur with certain prior art techniques. Whatever immunoassay technique is used, the results should be compared with the results using HPTLC to ensure that the technique which is selected does not substantially degrade the accuracy of the results.

Subject to this proviso, any known immunoassay technique can be tested for use with the present invention, such as the methods of antibody detection described in detail in Harlowe (1988), supra, Ausubel (1987; 1992), supra and Sambrook (1989), supra.

Applicants have not yet confirmed any theory as to why antisulfatide antibodies are found in the fluids of patients with such diverse conditions. Until there is any further evidence linking the results reported herein or confirming any given theory, no such theory would be accepted by the scientific community. Hypothetical theories which may or may not be applicable are that the antibodies in the sera of such patients and identified by the assay of the present invention are generated whenever a condition is initiated, co-initiated or exacerbated by an immune reaction to a viral invasion. If this were confirmed to be the case, the antibodies would be expected to be found in any autoimmune condition which may be triggered by an immune reaction, perhaps to an invading virus. This theory is supported by initial experimental results of the present laboratory (not shown) that the antibody of the present invention is also reactive against an antigen on the HIV envelope protein and possibly with other HIV viral proteins.

It should be further understood that while the antibody is denominated as "antisulfatide" and specific for the hydroxy fatty acid form of sulfatide, this denomination is based on the fact that the assay is conducted against chromatographically separated sulfatide molecules. There is no direct evidence that the antibodies were actually raised by an epitope on the hydroxy fatty acid form of sulfatide. The antibodies may have been initially triggered by a different but related sulfoglycolipid and are merely cross-reactive with the hydroxy fatty acid form of sulfatide. Thus, the use of the terminology antibody "against" a particular antigen, or the like, as appearing in the present specification and claims is specifically intended to comprehend antibodies which bind to or are reactive with such antigen regardless of whether or not that specific antigen was the original immunogen which caused the antibody to be raised.

EXAMPLE 1

METHOD FOR DETECTING THE PRESENCE OF ANTI-SULFATIDE ANTIBODIES AS AN INDICATOR OF HIV INFECTION

Sulfatide (Sigma, MO) (5 µg/lane) was applied to aluminum-backed Silica Gel 60 HPTLC plates (Merck, Darmstadt) and the plates were developed in chloroform/methanol/water (65:25:4, v/v/v). The plates were subsequently mixed in 0.15% polyisobutylmetachrylate in hexane for 30 seconds, dried, and blocked for 1 h in phosphate buffered saline (PBS) containing 2% bovine serum albumin (BSA) and 0.05% Tween-20. The plates were incubated with a 1:100 dilution of the respective sera samples from human patients known to be HIV positive or HIV negative according to a Western blot or DNA assay in PBS/BSA for 1 h at room temperature and washed extensively with PBS/Tween-20. The plates were then extensively washed as above, and incubated with peroxidase-labelled goat anti-human IgG (Boehringer Mannheim, Ind.) (1:400 dilution in PBS/BSA) for 1 h. After washing with PBS/Tween-20, reactivity towards sulfatide was visualized by incubating the plates in 0.01M sodium citrate, pH 6.0, containing 0.2 mg/ml 4-chloronaphthol and 0.03% $H_2O_2$.

As presented in FIGS. 10A–D, lanes a–c are control HIV-1 negative healthy individuals; lanes d and e are HIV-1 positive individuals, without fully developed AIDS; lane f is an HIV-1 positive patient with fully developed AIDS and demonstrated neurological involvement; and lane g is a sulfatide standard, chemically stained with the orcinol/$H_2SO_4$ spray reagent. The doublet is due to the presence of two sulfatide species containing non-hydroxy fatty acids (upper band) and hydroxy fatty acids (lower band) respectively. It can be seen that the practice bands in lanes d–f all correspond to the hydroxy fatty acid containing species. A method of the present invention was thus found to routinely and correctly diagnose human patients having no history of neurological or nephrological disease as HIV positive or negative.

EXAMPLE 2

ANTISULFATIDE ANTIBODY DETERMINATIONS IN THE DIAGNOSIS AND MANAGEMENT OF MULTIPLE SCLEROSIS

Methods:

Patient Population. Using proper informed consent procedures, a total of 178 samples were obtained for this study from patients with multiple sclerosis at different stages of the disease. This population includes patients under β-interferon and steroid treatments. A description of the MS population can be seen in Table 2. In addition, serial serum samples from 19 MS patients were taken at different time points of therapy. As controls, sera from 33 healthy controls and 90 random anonymous asymptomatic blood donors were included. Serum samples were also analyzed from patients with systemic lupus erythematosus (SLE), hepatitis, $RF^+$ and $HIV^+$ individuals. The designation of $RF^+$ denotes that the patients were rheumatoid arthritis patients with a positive indication of rheumatoid factor in their sera. Description of this latter patient population can be seen in Table 3.

TABLE 2

Serum Antisulfatide IgG in Multiple Sclerosis Patients

| MS Classification | Abbreviation | # of Samples | # Positive | % Positive |
|---|---|---|---|---|
| Chronic Progressive | CP | 68 | 60 | 88 |
| Chronic Stable | CS | 36 | 28 | 78 |
| Relapsing Progressive | RP | 19 | 15 | 79 |
| Relapsing Remitting | RR | 22 | 15 | 68 |
| Benign | B | 4 | 4 | 100 |
| HTLV-1 Positive | H | 2 | 1 | 50 |
| Optic Neuritis | ON | 5 | 2 | 40 |
| Unclassified | U | 22 | 19 | 86 |
| TOTAL | | 178 | 144 | 81 |

TABLE 3

Serum Antisulfatide IgG*

| Disease | Sample # | Positive | % Positive |
|---|---|---|---|
| $HIV^+$ | 37 | 33 | 89 |
| SLE | 11 | 9 | 81 |
| Hepatitis** | 9 | 5 | 56 |
| $RF^+$ | 5 | 5 | 100 |
| MS | 207 | 172 | 83 |
| Control*** | 123 | 20 | 16 |

*Analyses performed at 1:1000 dilution by TLC-immunostraining.
**The hepatitis samples included one sample which was also $HIV^+$. This sample was positive for antisulfatide IgG.
***The control samples included 33 of healthy controls and 90 samples from random asymptomatic blood donors.

Determination of Antisulfatide IgG. Measurement of antisulfatide IgG was performed by HPTLC immuno-staining. Sulfatide was applied onto an alumina-backed HPTLC plate and developed in chloroform/methanol/water (65:25:4, v:v:v). The plate was then fixed with 0.1% polyisobutylmethacrylate in hexane and blocked with 2% bovine serum albumin in 50 mM Tris-HCl, pH 7.6, 0.15M NaCl, 0.05% Tween-20 (TBST). The plate was then incubated with the test serum previously heat-inactivated at 56° C. for 30 min and diluted 1:1,000 in TBST for 1 hr at room temperature in polypropylene tubes. After washing with TBST, the plates were incubated with peroxidase conjugated anti-human IgG for 1 hr at room temperature, and washed as above. The presence of antisulfatide IgG was visualized by incubating the plate in 0.2 mg/ml 4-chloronaphthol in 10 mM sodium citrate, pH 6.0, 0.15M NaCl, 0.03% hydrogen peroxide. The intensity of the staining reaction was visually determined using a scale of 0 to 4 by two independent observers.

Results:

Of 123 control specimens studied, 20 (16%) were positive for the presence of antisulfatide antibody. 17 samples were positive from the anonymous asymptomatic blood donor population and 3 samples from the known healthy control population. Of these 3 latter positive samples, one was from an apparently healthy adult male who had Campylobacter infection one month prior to testing of his serum. A follow up serum specimen obtained one year later was negative. The second specimen was that of an adult male with a history of autonomic disturbance of bladder dysfunction and the third was from a hospitalized adult female with aseptic meningitis.

Figure 2:
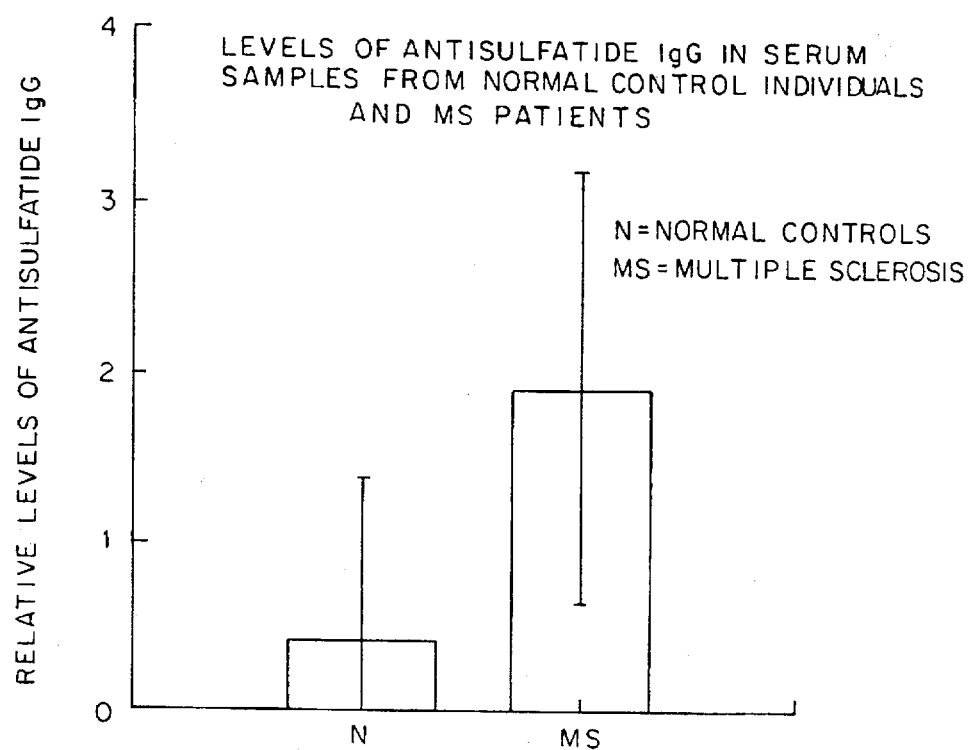
FIG. 2 is a graph showing the levels of antisulfatide IgG in serum samples from normal controlled individuals and MS patients.
Figure 7:
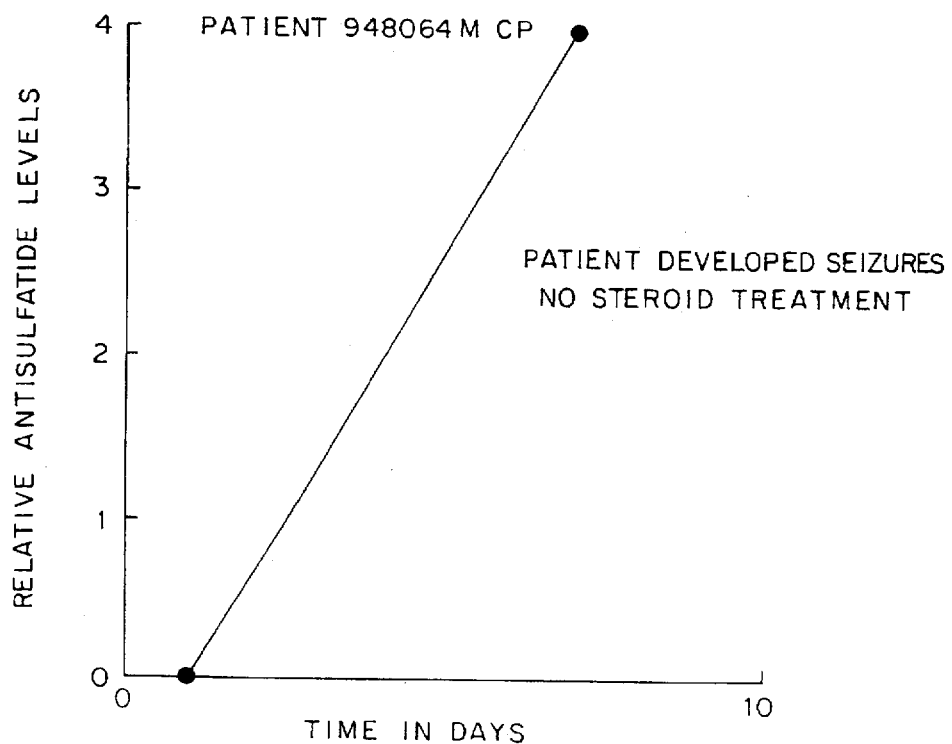
Figure 8:
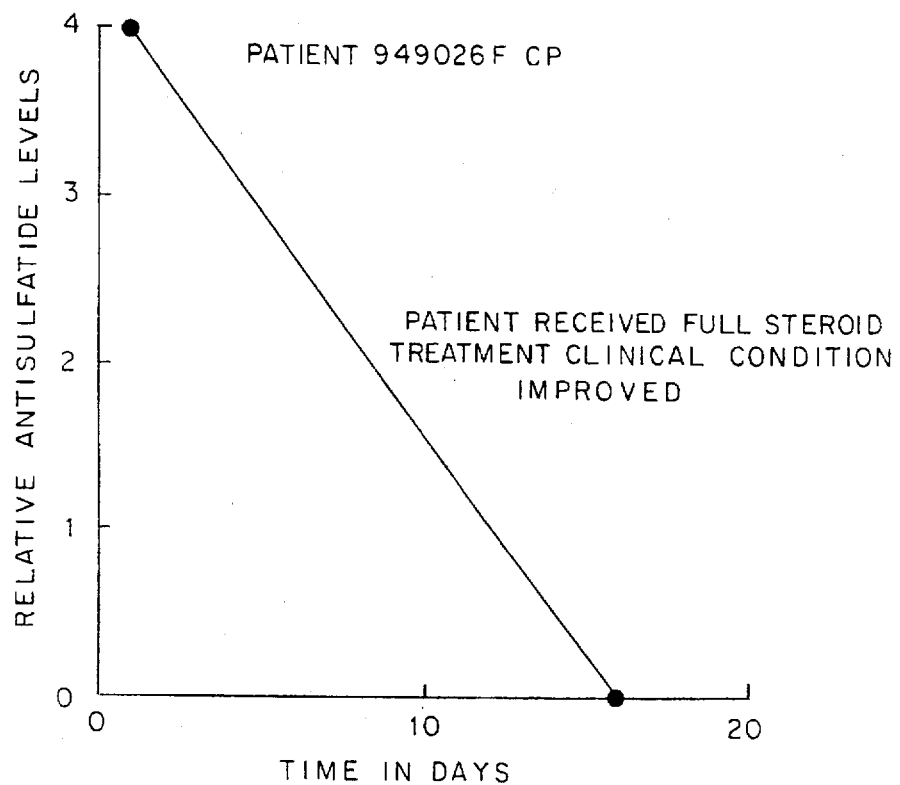
Figure 9:
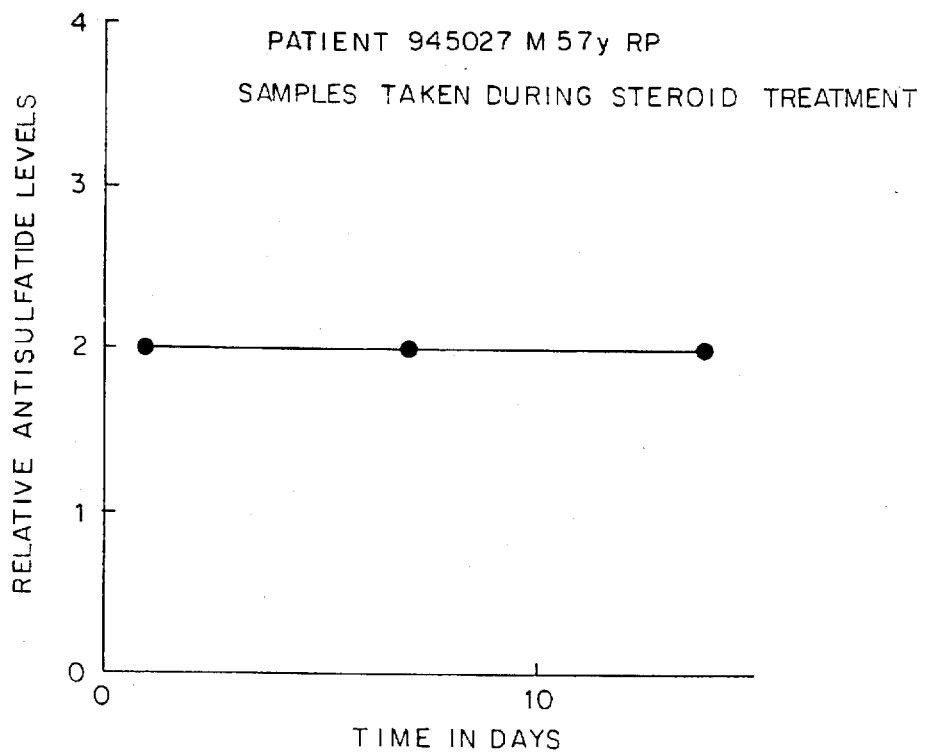

Serum antisulfatide IgG was present in 143/178 samples from multiple sclerosis patients. The results are summarized in tables 2 and 3. Comparison of the antisulfatide IgG levels between the control and MS populations indicated a statistically significant difference (p<0.05) (FIG. 2). In general, the chronic form of the disease gave a consistently higher reaction than did the other diagnostic categories. In patients with optic neuritis (ON), which in some patients is the first sign of the disease, 2/5 patients were positive for the presence of antisulfatide IgG under the conditions tested. One of the three negative specimens was from a patient who had recovered from a single attack of optic neuritis one year earlier. It is not known at this point which if any of the five ON patients tested went on to develop MS. With steroid treatment in some MS patients, there appeared to be a decrease in the levels of antisulfatide IgG associated with this form of therapy. See FIGS. 3–6 and 8. However, in some other patients, it was not clear that this was the case (see FIG. 9). It is believed, however, that longer term study will confirm the quantitative correlation of antisulfatide antibody titer with efficacy of treatment. FIG. 7 shows the increase in antisulfatide level over time in an MS patient suffering from worsening clinical condition.

Antisulfatide IgG was also found in $HIV^+$ (89%) as well as in SLE (81%) patients and $RF^+$ (100%) individuals. These data are given in Table 3. This table also shows the antisulfatide IgG in 56% of the hepatitis patients studied.

Conclusions:

1. Higher levels of antisulfatide IgG preferential for the hydroxy fatty acid forms of sulfatide are present in 83% of patients diagnosed with multiple sclerosis as compared to control populations. Since the MS population sample included individuals who were under treatment with either β-interferon or steroids, the percent of positivity in MS patients is suspected to be initially higher.

2. Higher levels of antisulfatide IgG preferential for the hydroxy fatty acid forms of sulfatide are present in 100% of patients diagnosed with rheumatoid arthritis and 81% of patients diagnosed with SLE as compared to control populations.

3. In some patients a decrease in the antisulfatide IgG levels seems to be associated with the steroid treatment and in the improvement of the clinical condition of the patient. However, in some patients this response to steroids was not observed in the serum samples analyzed.

In summary, a high degree of positivity for antisulfatide IgG in the sera of patients with multiple sclerosis, rheumatoid arthritis and SLE has been demonstrated, as well as in $HIV^+$ individuals. In contrast, the antibody is detected with much less frequency in the sera of control individuals.

EXAMPLE 3

INTRATHECAL SYNTHESIS OF ANTISULFATIDE IgG IS ASSOCIATED WITH PERIPHERAL NERVE DISEASE IN THE ACQUIRED IMMUNODEFICIENCY SYNDROME

Materials and Methods:

Serum and CSF collection. Sera were obtained from 37 HIV seropositive ($HIV^+$) individuals. These included asymptomatic individuals, individuals with mild cognitive and/or motor dysfunction and individuals with AIDS and CNS degeneration. Cerebrospinal fluid obtained in the course of diagnostic evaluations was derived from 11 of the above individuals and from 17 additional $HIV^+$ individuals. Three of these CSF samples were from $HIV^+$ individuals with neurosyphilis. The 123 HIV seronegative ($HIV^-$) control samples included sera form 33 known healthy individuals and 90 randomly chosen samples from asymptomatic blood donors. The CSF samples used as controls were from 18 $HIV^-$ individuals undergoing testing for other unrelated neurological conditions. The specimens were routinely heat inactivated at 56° C. for 30 minutes prior to use.

Glycolipids. Bovine brain sulfatide and galactosylceramide were obtained from Sigma Chemical Company, St. Louis, Mo. A mixture of sulfatide and lactosylceramide sulfate was also obtained from the urine of a two year old boy with late-infantile metachromatic leukodystrophy. Sulfogalactosyldiglyceride (seminolipid) was obtained from HSC, Toronto, Canada. Lysosulfatide was prepared from sulfatide by removal of the fatty acid moiety with alkaline base hydrolysis (Dubois et al., *Anal. Biochem.*, 102:313–317 (1980)). Sulfoglucuronyl-paragloboside was kindly donated by Dr Firoze Jungalwala, Shriver Center, Waltham, Mass.

TLC immunostaining. Sulfatide (5 μg/lane) was applied on aluminum backed Silica Gel 60 HPTLC plates (Merck) and the plate developed in chloroform/methanol/water 65:25:4 (v:v:v). The plate was cut into individual strips and fixed 30 seconds in 1.5% polyisobutylmethacrylate in hexane. The strips were than blocked 30 minutes in 50 mM Tris HCl, pH 7.6, 0.15M NaCl, 0.05% Tween-20 (TBS/Tween) containing 2% BSA. Each strip was then incubated with the test serum diluted in TBS/Tween for 1 hr at room temperature. The strips were washed with TBS/Tween and incubated 1 hr with peroxidase-labeled goat anti-human IgG (Jackson Laboratories, Pa.) and washed as above. The strips were then incubated with 0.2 mg/ml 4-chloronaphthol in 10 mM Na citrate, pH 6.0, 0.03% hydrogen peroxide. For the antigenic specificity studies, the glycolipids indicated in FIG. 1 were applied in equimolar amounts on the HPTLC plate which was then developed in chloroform/methanol/water 60:32:7 (v:v:v). The determination of the IgG isotype was performed as above except that peroxidase-conjugated monoclonal anti-human IgG1, IgG2, IgG3, and IgG4 (The Binding Site, Birmingham, UK) were used as second antibodies. Peroxidase conjugated goat anti-human kappa and lambda light chains used to determine the nature of the light chain of the antisulfatide IgG were obtained from Fisher Scientific. Chemical staining of the glycolipids was performed with the orcinol-$H_2SO_4$ spray reagent.

Purification of antisulfatide IgG. The antibody was purified from 190 ml of heat inactivated serum from a healthy $HIV^+$ individual. The IgG fraction was precipitated with 33% ammonium sulfate and purified by ion-exchange chromatography. The sulfatide coated-octyl Sepharose affinity column was prepared as described in Hirabayashi et al., *J. Biochem.*, 94:327–330 (1983). An aliquot of the IgG fraction (about 80 mg protein) was applied onto the column which was then extensively washed with PBS. The bound IgG fraction was eluted with 3M Na thiocyanate in PBS and immediately dialyzed against PBS.

Immunocytochemical analysis of human brain tissue. Immunocytochemical staining with the affinity purified antisulfatide IgG was performed on frozen human brain section. The tissue sections were incubated for 1 h in 10% normal goat serum (NGS) in PBS followed by an overnight incubation with the affinity purified antisulfatide-IgG diluted 1:500 in PBS containing 2% NGS. After three washes in PBS, the sections were incubated for 5 hours with peroxidase conjugated anti-human IgG (1:300 dilution in PBS/2% NGS). After washing as above, the sections were incubated with 1 mg/ml 3,3'-diaminobenzidine and 0.005% hydrogen peroxide in 0.05M Tris-HCl, pH 7.6 containing 10% (v/v) imidazole. To remove lipids prior to immunochemical staining the sections were pretreated with chloroform/methanol 2:1 as described in Wikstrand et al., *J. Neuropathol. Exp. Neurol.*, 50:756–769 (1991).

Results and Discussion:

This experiment was designed to assess the presence in serum and CSF of antibodies directed against sulfatide, a major glycolipid component of myelin whose structure is closely related to that of galactosylceramide (see FIG. 1 for structures). A semi-quantitative high performance thin layer chromatography (HPTLC)-immunostaining method was favored to detect antisulfatide antibodies in biological fluids over other more quantitative procedures, such as enzyme-linked immunoadsorbent assays (ELISA), because the HPTLC-immunostaining method yielded no false positive results caused by the cross-reactivity of some sera with the blocking agent. Under the present assay conditions, samples were considered to be positive for antisulfatide antibodies when titers were equal to or greater than either 1:1,000 or 1:100 for serum and cerebrospinal fluid, respectively.

Serum samples were first analyzed from HIV-seropositive individuals and from HIV-seronegative controls with no apparent symptomatology or with non-AIDS related pathologies. Thirty three out of 37 HIV seropositive individuals (89%) tested positive at 1:1,000 dilution for the presence of serum antisulfatide IgG. In contrast, 20 of 123 sera (16%) from asymptomatic HIV seronegative controls tested positive for the antibody. The association between HIV seropositivity and presence of serum antisulfatide antibodies was statistically significant (two-tailed p<0.01, Chi square with Yates correction and Fisher's exact test). Nonetheless, among HIV-seropositive individuals, serum antisulfatide IgG levels showed no correlations with clinical status parameters (CDC staging or CD4 T cell counts).

In addition, 8 out of 25 HIV-seropositive individuals with neurological complications tested positive for CSF antisulfatide IgG (titer >1:100). None of 18 age-matched HIV-seronegative controls (including 5 asymptomatic, 5 with multiple sclerosis, one with SLE, 2 with stroke, 2 with laryngeal carcinoma, 2 with diabetic polyneuropathy, and one with subarachnoid hemorrhage) tested positive for CSF antisulfatide IgG. The association between CSF antisulfatide antibody positivity and HIV infection with neurological complications was statistically significant (two-tailed p<0.01, Chi square with Yates correction and Fisher's exact test) when compared to HIV-seronegative individuals. Although HIV-infected individuals with no neurological complications would have been a more preferable reference group, CSF samples were not available for this type of individuals because of lack of clinical indication to obtain them. The 25 HIV-infected individuals with neurological complications were then stratified according to the presence of either predominantly central (18 individuals) or peripheral (7 individuals) nervous system disease. Analysis of the HIV-infected individuals stratified in this way, showed a significant association between presence of CSF antisulfatide antibody and peripheral nervous system involvement (6/7 with peripheral as compared to 2/18 HIV-infected individuals with predominantly central nervous system disease, p=0.03, Chi square test with Yates correction and p=0.015, Fisher's exact test). Two out of 3 additional HIV-infected individuals with neurosyphilis showed CSF antisulfatide positivity.

The statistical significance of the association between HIV infection with neurological complications and CSF antisulfatide antibody positivity, as well as the presence of CSF antisulfatide antibody positivity in AIDS patients with neurosyphilis, prompted the determination of whether antisulfatide antibodies were synthesized intrathecally or were derived from peripheral blood through blood-brain barrier leakage. Paired serum and cerebrospinal fluid samples from 11 HIV-seropositive individuals were analyzed. The CSF/serum ratio of total IgG were used to standardize CSF/serum antisulfatide antibody ratios (Table 4). A standardized CSF/serum ratio of up to 1 could be accounted for by peripheral blood leakage into the CSF compartment, while a standardized ratio greater than 1 is indicative of intrathecal synthesis of antibodies. Out of the 11 samples analyzed, 4 CSF samples had antisulfatide antibody positivity. Out of the latter 4, three with normalized CSF/serum antisulfatide antibody ratios greater than 10 corresponded to individuals with predominantly peripheral nervous system disease (one with ascending radiculopathy, a second one with peripheral neuropathy and dementia, and the third one with sensory loss below knee in stocking distribution in the left leg). The fourth individual with CSF antisulfatide antibody positivity but normalized CSF/serum ratio of less than 1, corresponded to an AIDS individual with neurosyphilis. Higher levels of antibody in the CSF were observed and appeared to correlate with peripheral neuropathy.

TABLE 4

Antisulfatide IgG Levels and Standardized Antisulfatide IgG Ratios in AIDS Patients with Neurological Involvement

| # | Diagnosis | Predominant neurological disease | AS* IgG in CSF Titer | CSF IgG mg/dL | AS IgG in Serum Titer | Serum IgG mg/dL | Standardized AS Ig Ratios (CSF/Serum)[b] |
|---|---|---|---|---|---|---|---|
| 1 | ascending radiculopathy | Peripheral | 1:100 | 2.8 | 1:1,000 | 730 | 26 |
| 2 | peripheral neuropathy, dementia | Peripheral | 1:1,000 | 89.1 | 1:1,000 | 1163 | 13 |
| 3 | sensory neuropathy left leg | Peripheral | 1:100 | 2.3 | 1:10,000 | 2397 | 10 |
| 4 | neurosyphilis | Peripheral | 1:100 | 137.0 | 1:10,000 | 3815 | 0.3 |
| 5 | dementia | Central | <1:100 | 7.8 | 1:1,000 | 942 | 0 |

TABLE 4-continued

Antisulfatide IgG Levels and Standardized Antisulfatide IgG Ratios in AIDS Patients with Neurological Involvement

| # | Diagnosis | Predominant neurological disease | AS* IgG in CSF Titer | CSF IgG mg/dL | AS IgG in Serum Titer | Serum IgG mg/dL | Standardized AS Ig Ratios (CSF/Serum)[b] |
|---|---|---|---|---|---|---|---|
| 6 | seizures | Central | <1:100 | 10.3 | 1:100 | 2024 | 0 |
| 7 | seizures, liver carcinoma | Central | <1:100 | 10.9 | 1:1,000 | 2949 | 0 |
| 8 | minor brain atrophy | Central | <1:100 | 8.4 | 1:100 | ND[c] | 0 |
| 9 | headaches | Central | <1:100 | 6.8 | 1:10,000 | 1667 | 0 |
| 10 | B-cell lymphoma, multiple brain lesions | Central | <1:100 | 7.1 | 1:10,000 | 2122 | 0 |
| 11 | seizures, dementia | Central | <1:100 | 4.3 | 1:100 | 1215 | 0 |

[a]Antisulfatide;
[b]Standardized AS IgG ratios = (AS IgG in CSF/AS IgG in serum)/(Total IgG in CSF/Total IgG in serum);
[c]Not done Based on the results presented above, CSF antisulfatide antibody positivity in CSF/serum ratios greater than 10 is therefore significantly associated with peripheral nervous system disease in HIV-infected individuals (two-tailed $p \leq 0.01$, Chi square with Yates correction and Fisher's exact test). The remaining 7 paired samples, with serum but not CSF antisulfatide antibody positivity, corresponded to HIV-infected individuals with predominantly central nervous system involvement. These results illustrate the protective role of the blood-brain barrier to the peripheral nervous system-oriented effects of antisulfatide antibodies in the CSF compartment. However, an event causing disruption in the blood-brain barrier would allow leakage of antisulfatide antibody into the CSF compartment from the peripheral blood as was observed in the AIDS patient with neurosyphilis.

Figure 3:
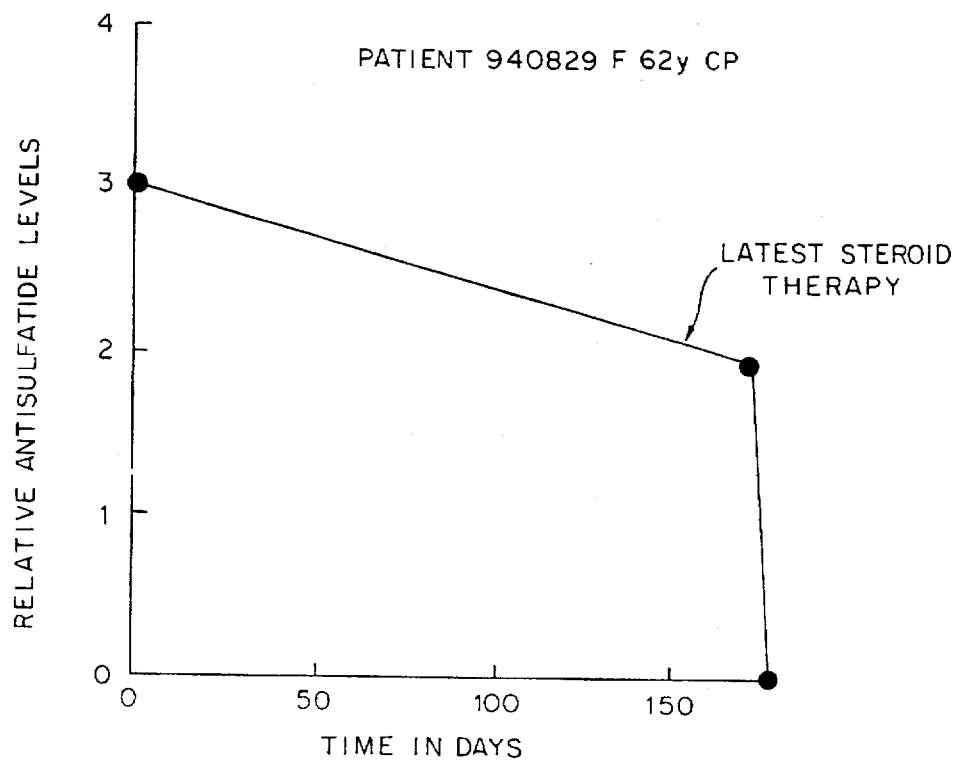
FIGS. 3–9 are graphs showing patient monitoring data, as represented by relative antisulfatide levels as a function of time, for seven different patients at days noted with or without therapy as noted. The clinical course can be seen in some instances.
Figure 4:
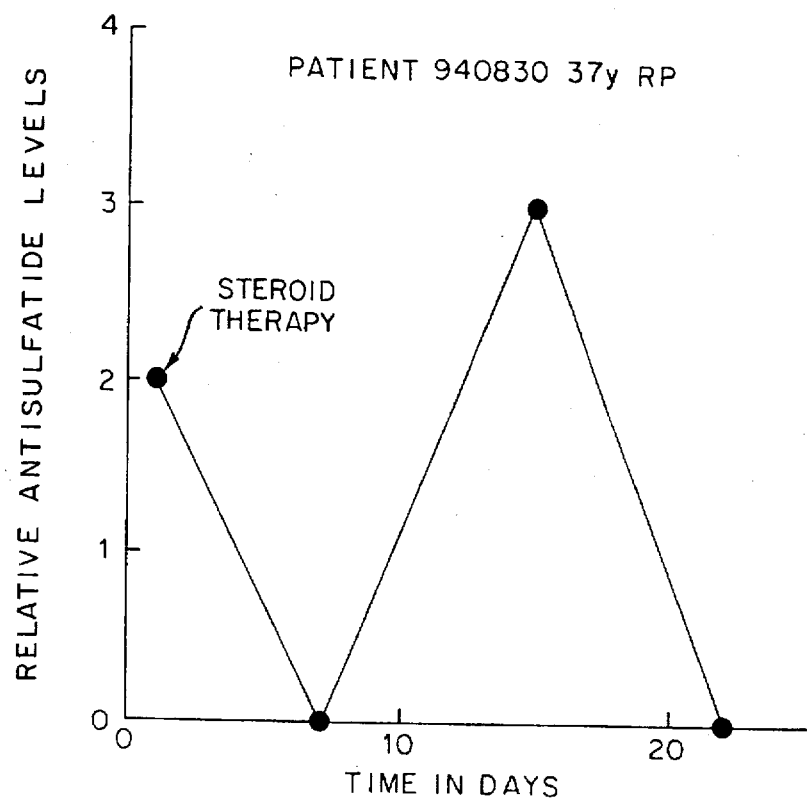
Figure 5:
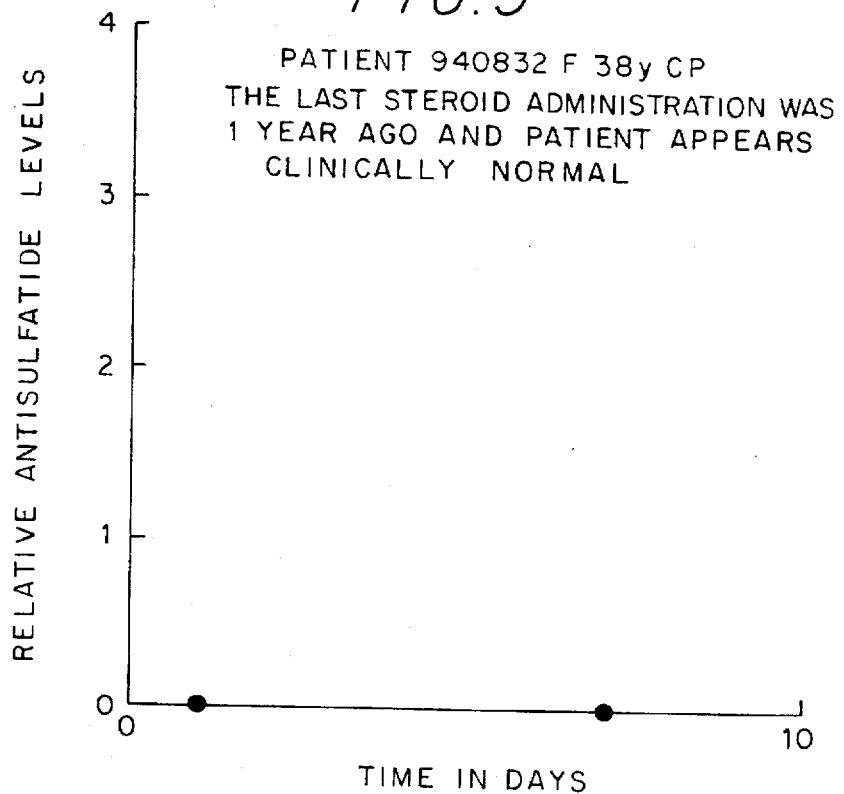
Figure 6:
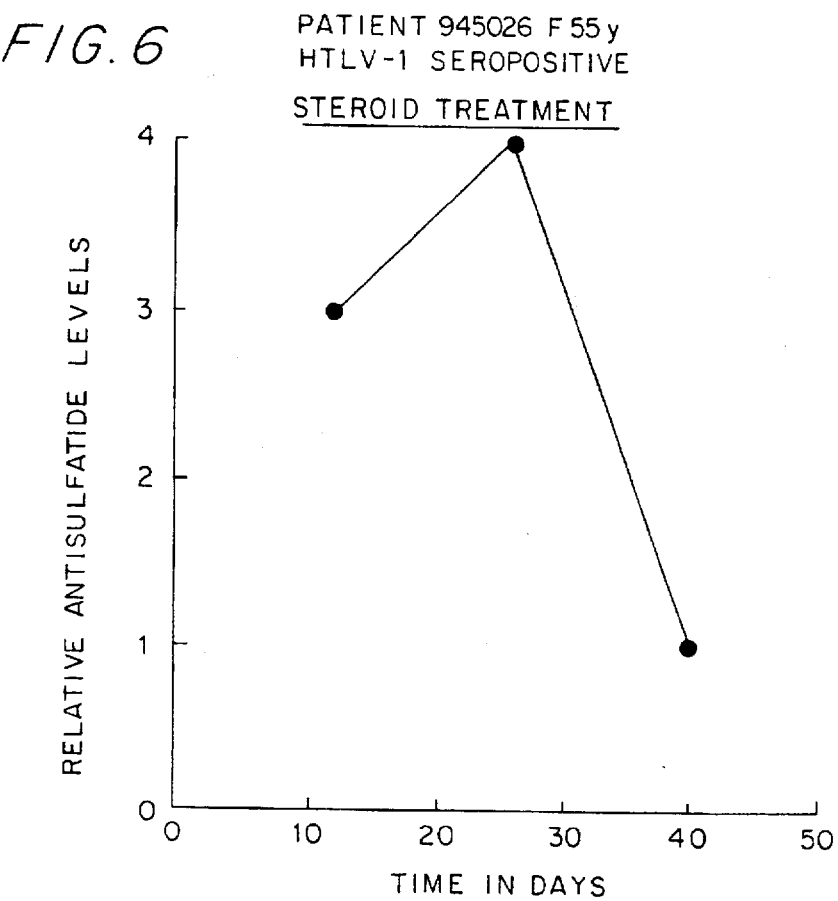

To further characterize the antisulfatide IgG, antibody was purified by affinity chromatography through octyl-Sepharose coated with sulfatide (Hirabayashi (1983), supra). Serum, but not CSF, from an HIV-infected individual was used for the antibody affinity purification due to sample size limitations. The antigenic specificity was examined by HPTLC immunostaining using the glycolipids indicated in FIG. 1. Both the original serum and the affinity purified IgG were analyzed and showed the same specificity. The results of this analysis are shown in FIG. 3, panels C (serum) and D (affinity purified IgG). The antisulfatide IgG reacted equally well with bovine brain sulfatide (lane b) and human sulfatide prepared from the urine of a patient with metachromatic leukodystrophy (lane e, upper band). It also recognized lactosylceramide sulfate (lane e, lower band) and to a lesser extent, sulfogalactosyldiglyceride (seminolipid) (lane d). It did not react with the non-sulfated parent compound galactosylceramide (lane a), suggesting that galactose 3-sulfate is part of the epitope recognized by the antibody. As mentioned above, the antibody reacted preferentially with the hydroxy-fatty acid containing form of sulfatide. No reaction was detected with lysosulfatide (lane c) indicating that the fatty acid is important for binding, while changes in the type of lipid moiety, as in the seminolipid, greatly reduced but did not abolish the reactivity. Reactivity towards lactosylceramide sulfate, in which the galactose is not directly attached to ceramide, is due to the conformation of this glycolipid which brings the galactose-3-sulfate and the ceramide as close as in the sulfatide molecule (Fredman et al., Biochem. J., 251:17–22 (1989)). No reactivity could be detected with sulfoglucuronylpara-globoside, a sulfated glycolipid found in PNS myelin (Chou et al., J. Biol. Chem., 261:11717–11725 (1986), Ilyas et al., J. Neuroimmunol., 37:85–92 (1992)) (results not shown). The antisulfatide antibody was recognized by anti-κ and anti-λ light chain antibodies suggesting its polyclonal nature. Isotype determination indicated that the antisulfatide antibody was predominantly of the IgG1 type.

To establish whether the antisulfatide IgG could recognize and bind to its antigen in situ, frozen human brain sections were immunostained with the affinity purified antibody. The antibody was found to stain preferentially oligodendrocytes and their processes associated with axons in the human pontine white matter. Pre-treatment of the sections with chloroform/methanol (2:1) to remove glycolipids, greatly reduced the staining, suggesting that the main target of the antibody in the section was indeed a glycolipid in nature. The preferential staining of the oligodendrocytes was consistent with the high levels of sulfatide in these cells (Norton et al., J. Neurochem., 21:759–773 (1973)).

In terms of the mechanisms for antisulfatide antibody-mediated pathogenesis, it is worth mentioning that sulfatide, besides being a major component of myelin (Norton et al. (1973), supra), is also present in the kidney and at lower concentrations in spleen, erythrocytes, granulocytes, platelets, endothelial cells, stomach, intestine and testis (Ginsburg et al., Biochimie, 70:1651–1659 (1988)). Sulfatides have been suggested to play a role in the $Na^+$ transport (Zalc et al., FEBS Lett., 92:92–96 (1978)), in the binding of opiates to their receptor (Graves et al., Science, 207:75–76 (1980)), and in cell adhesion. Several proteins including properdin (Holt et al., J. Biol. Chem., 265:2852–2855 (1990)), factor XI 1, the adhesive glycoproteins laminin, thrombospondin and von Willebrand factor (Ginsburg et al. (1988), supra) and the members of the selectin family L-selectin/LECAM (Suzuki et al., Biochem. Biophys. Res. Comm., 190:426–434 (1993)) and CD62/P-selectin (Aruffo et al., Cell, 67:35–44 (1991)) have been found to interact with sulfatide. The fact that sulfatide is a major component of myelin and is also involved in cell adhesion suggests that the antisulfatide antibody in the cerebrospinal fluid of AIDS patients has the potential to induce myelin damage and to inhibit cell function by interference with the binding of sulfatide to its ligands.

The antisulfatide antibodies detected in the CSF of AIDS patients with PNS disease are probably synthesized intrathecally by infiltrating peripheral blood cells. On the other hand, the presence of CSF antisulfatide in patients with neurosyphilis mimics the findings in rabbits where the blood-nerve barrier is defective at the dorsal root ganglia and the nerve root (Ozawa et al., *Acta. Neuropathol.*, 77:621–628 (1989)). Further research should elucidate the histopathogenesis of PNS demyelination associated with HIV infection and the presence of antisulfatide antibodies.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the generic concept of the present invention. Therefore, such adaptations and modifications are intended to be comprehended within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein.

What is claimed is:

1. A method of screening for or diagnosing a condition selected from the group consisting of multiple sclerosis, HIV infection, rheumatoid arthritis and systemic lupus erythematosus in a subject, comprising:

assaying in vitro a tissue or body fluid sample of a subject suspected of having one of said conditions, for the presence of IgG against the hydroxy-fatty acid containing form and level of sulfatide, whereby the presence of IgG levels substantially above those in healthy controls is indicative of an increased likelihood that the subject has one of said conditions.

2. A method in accordance with claim 1 of screening for or diagnosing multiple sclerosis, wherein said tissue or body fluid sample is from a subject suspected of having multiple sclerosis, whereby the presence of said IgG levels substantially above those in healthy controls is indicative of an increased likelihood that the subject has multiple sclerosis.

3. A method in accordance with claim 1 of screening for or diagnosing HIV infection, wherein said tissue or body fluid sample is from a subject suspected of having HIV infection, whereby the presence of said IgG levels substantially above those in healthy controls is indicative of an increased likelihood that the subject has HIV infection.

4. A method in accordance with claim 1 of screening for or diagnosing rheumatoid arthritis, wherein said tissue or body fluid sample is from a subject suspected of having rheumatoid arthritis, whereby the presence of said IgG levels substantially above those in healthy controls is indicative of an increased likelihood that the subject has rheumatoid arthritis.

5. A method in accordance with claim 1 of screening for or diagnosing systemic lupus erythematosus, wherein said tissue or body fluid sample is from a subject suspected of having systemic lupus erythematosus, whereby the presence of said IgG levels substantially above those in healthy controls is indicative of an increased likelihood that the subject has systemic lupus erythematosus.

6. A method in accordance with claim 1, wherein said assay is by means of high performance thin layer chromatography.

7. A method in accordance with claim 2, wherein said assay is by means of high performance thin layer chromatography.

8. A method in accordance with claim 3, wherein said assay is by means of high performance thin layer chromatography.

9. A method in accordance with claim 4, wherein said assay is by means of high performance thin layer chromatography.

10. A method in accordance with claim 5, wherein said assay is by means of high performance thin layer chromatography.

11. A method in accordance with claim 1, wherein said assaying step comprises assaying for the presence of IgG which is selective to the hydroxy-fatty acid containing form of sulfatide as compared to the non-hydroxy-fatty acid containing form of sulfatide.

12. A method for monitoring the course or efficacy of treatment of selected from the condition selected from the group consisting of multiple sclerosis, rheumatoid arthritis and systemic lupus erythematosus, comprising:

assaying in vitro a tissue or body fluid sample of a subject having one of said conditions for the presence of IgG against the hydroxy-fatty acid containing form of sulfatide, whereby the presence of said IgG levels substantially above those in healthy controls is quantitatively representative of the stage or severity of said condition.

13. A method in accordance with claim 12, wherein said condition is multiple sclerosis.

14. A method according to claim 13 for monitoring the course or efficacy of treatment of a patient having multiple sclerosis, wherein said assaying step is conducted on a tissue or body fluid sample of a patient undergoing said treatment at two or more times in the course of said treatment, whereby the relative antibody titer found in each assay is representative of the course or efficacy of said treatment.

15. A method in accordance with claim 12, wherein said assaying step comprises assaying for the presence of IgG which is selective to the hydroxy-fatty acid containing form of sulfatide as compared to the non-hydroxy-fatty acid containing form of sulfatide.

* * * * *